United States Patent [19]

Drake, Jr.

[11] Patent Number: 4,664,664

[45] Date of Patent: May 12, 1987

[54] BALLISTIC PROJECTILE

[75] Inventor: James F. Drake, Jr., Minneapolis, Minn.

[73] Assignee: Minnesota Mining and Manufacturing Company, St. Paul, Minn.

[21] Appl. No.: 772,198

[22] Filed: Sep. 4, 1985

Related U.S. Application Data

[63] Continuation of Ser. No. 265,468, May 20, 1981, abandoned, which is a continuation of Ser. No. 740,665, Nov. 10, 1976, abandoned.

[51] Int. Cl.[4] .......... A61M 5/00

[52] U.S. Cl. .......... 604/891; 604/49; 102/502; 102/512

[58] Field of Search .......... 604/891, 49; 102/512, 102/502, 529, 501; 273/428

[56] References Cited

U.S. PATENT DOCUMENTS

| | | | |
|---|---|---|---|
| 721,050 | 2/1903 | Kersey | 102/529 |
| 1,230,712 | 6/1917 | Holter | 42/78 |
| 1,241,409 | 9/1917 | Lizarraga | 102/501 |
| 1,275,028 | 8/1918 | Holter | 42/78 |
| 3,790,948 | 2/1974 | Ratkovich | 343/113 R |
| 3,902,683 | 9/1975 | Bilsbury | 102/529 X |
| 3,948,263 | 4/1976 | Drake et al. | 128/260 |
| 3,982,536 | 9/1976 | Krogseng et al. | 128/260 |
| 4,065,753 | 12/1977 | Paul | 340/152 T |
| 4,087,791 | 5/1978 | Lemberger | 340/152 T |

FOREIGN PATENT DOCUMENTS

| | | | |
|---|---|---|---|
| 1253485 | 1/1961 | France | 102/529 |
| 2410 | of 1856 | United Kingdom | 244/3.23 |
| 1645 | of 1857 | United Kingdom | 244/3.23 |

OTHER PUBLICATIONS

Greener, W. W. "The GUN and its Development", 8th ed. pp. 614–619 (1907).

Boothroyd, "Guns Through the Ages", pp. 80–87, (1961).

*Primary Examiner*—Michael H. Thaler

*Attorney, Agent, or Firm*—Donald M. Sell; James A. Smith; Warren R. Bovee

[57] ABSTRACT

Ballistic projectiles for subsonic propulsion having a helically twisted body portion and a tapered nose portion and having an apparent density of up to 5 g/cm$^3$. The projectiles can be propelled through barrels having a complementary barrel without objectionable fouling.

20 Claims, 7 Drawing Figures

BALLISTIC PROJECTILE

This is a continuation of application Ser. No. 265,468 filed May 20, 1981 abandoned, which is a continuation of application Ser. No. 740,665 filed Nov. 10, 1976, abandoned.

The present invention relates to sub-sonic ballistic projectiles having a unique combination of body shape and apparent density. The projectiles can be propelled from a smooth bore barrel with spin about the longitudinal axis imparted thereto. Due to their physical and ballistic characteristics the projectiles are particularly suited for the ballistic impact on and/or implantation in living animal bodies.

Ballistically implantable projectiles containing biologically active materials for implantation into living animal bodies have been disclosed in U.S. Pat. No. 3,948,263 issued Apr. 6, 1976, and U.S. Pat. No. 3,982,536 issued Sept. 28, 1976. These projectiles inherently have a low apparent density and provide the capability of obtaining precisely controlled ballistic implantation within a target, such as an animal body. However, the low density materials used in these ballistic projectiles cause fouling problems when shot through conventional land and groove barrels which provide spin stabilization of the projectiles.

The present invention overcomes the fouling problem associated with the known ballistically implantable projectiles by providing a projectile having a unique combination of helical body shape and apparent density. These projectiles can be projected from a barrel having a smooth, helical bore in a spinning mode, preferably with sufficient spin about the longitudinal axis to stabilize the flight of the projectile, by a mechanical or expanding gas propulsion means without objectionable fouling of the barrel.

Prior to the present invention, lead projectiles having helically shaped polygonal bodies were used to achieve extreme accuracy in target rifles and other firearms. British Pat. No. 2410 issued in 1855 and Pat. No. 1645 issued in 1857 show the use of lead bullets having a helical polygonal body and a complementary helically bored barrel. Articles treating the history of guns and bullets discuss these firearm systems. Of interest is the book "Guns through the Ages" by Geoffrey Boothroyd, Crown Publishers, Inc., (1968), (Lib. Congress, Cat. Card No. 62-15152), at pages 80-85, which describes the Whitworth hexagonal twisted bore and the Lancaster twisted oval bore.

The Whitworth rifles, while being extremely accurate, were not favored since the rifle "fouled very badly after about 2 shots" ("Guns", supra, 84) and required a special scraper to clean the bore after each shot. Accordingly, it is quite surprising that the projectiles of this invention do not cause objectionable fouling when propelled through a complementary barrel.

The ballistic projectiles of this invention comprise an elongated body portion and a tapered nose portion. The projectile body has a configuration which can be geometrically inscribed longitudinally within the volume enclosed by an imaginary solid helix generated by revolving a non-circular plane figure at a constant rate around an axis contained within and perpendicular to the plane of the figure while simultaneously moving the plane figure along the perpendicular axis at a constant rate. The imaginary helical volume thus has a constant pitch. The axis is preferably at the geometric center of the plane figure.

The plane figure used to generate the helical volume must have a non-circular perimeter wherein all extended, imaginary, straight lines circumscribing, i.e. tangent to, the perimeter of the plane figure intersect at a point on or outside of the perimeter. At least the bearing surface portions of the inscribed projectile, i.e. those surfaces which adjoin the surface of the helical volume, have the contour of the helical volume. Preferably, the body of the projectile is constructed so that no open path exists, within the helical volume, which extends along the complete length of the projectile body. That is, the projectile body plugs or seals the helical volume so as to prevent the passage of another body or material therethrough. This is necessary when the projectile is to be propelled by an expanding gas propulsion means so that the projectile body can "seal" the complementary barrel to prevent gas leakage therethrough. With mechanical propulsion means the sealing feature is not a necessity.

Further, the projectile must have a relatively low apparent density. The apparent density should be about 5 grams/cm$^3$ or less. Preferably the apparent density will range from about 1 to about 3 grams/cm$^3$ and most preferably from about 2 to about 3 g/cm$^3$. The apparent density is obtained by dividing the total mass of the projectile, in grams, by the apparent volume, in cubic centimeters. The apparent volume is the volume contained within the exterior surface of the projectile, including the volume of cavities and voids formed within the projectile, even though such cavities may communicate with the exterior of the projectile. Thus, the apparent volume of a projectile having a cavity opening to the rear of the projectile is the same as the volume occupied by a completely solid projectile having the same exterior configuration and dimensions. Merely adding a cavity to, or creating voids in, the projectile does not change the apparent volume as defined herein.

Advantageous results are obtained when the projectiles of this invention are propelled, at subsonic muzzle velocities, through a complementary barrel, that is, a barrel having a helically twisted bore of the same configuration and dimension as the imaginary helical volume circumscribing the projectile to be propelled through the barrel, the bore of the barrel being free of the internal projections contained in conventional land and groove barrels.

In one embodiment of the projectile, the helical volume in which the projectile is inscribed is formed by the rotation of a polygon, preferably a regular polygon, figure around and along the axis as described. The projectiles according to this embodiment would have a body surface comprising a plurality of planar sides twisted around the longitudinal axis of the body to form a helical polyplanar body surface.

In an alternative embodiment of the invention the helical volume in which the projectile is inscribed is formed by rotation of a curved, non-circular figure, such as an ellipse, around the axis as described hereinabove. This provides a projectile having a helically curved body surface analogous to a threaded bolt, screw, twist drill or similar helically shaped article.

In yet another embodiment, the helical volume in which the projectile is inscribed is formed by the rotation of a plane figure having both curved and straight perimetric portions. Such an embodiment provides a projectile having at least one "flat" or planar portion helically twisted around and along the projectile.

As used herein the term non-circular means that the perimeter is not a complete, perfect circle. It is contemplated, however, that portions of the perimeter may comprise arcs having a constant radius including embodiments wherein the plane generating figure described hereinabove has one or more straight sides but is otherwise circular. Thus, the term non-circular includes a variety of curved perimeters, polygonal, triangular and rectangular perimeters, as well as perimeters having combinations of curved and straight portions.

The projectiles can be constructed to carry a variety of payloads if desired. They are particularly useful for treating and/or labeling animals by ballistic contact with or implantation in the animal. When used for the treatment of animals, the projectiles may be made to carry one or more of a variety of biologically active materials such as vitamins, minerals, tranquilizers, antigens and the like. The projectile and/or its contents may be formulated or structured to provide either or both of delayed or sustained release of the biologically active contents. The projectile may also contain an identification or labelling element such as a dye or other coloring means or electronic detection elements.

BRIEF DESCRIPTION OF THE DRAWING

Referring now to FIG. 1, there is shown a projectile 10 comprising elongated body 12 and tapered nose 14. Body 12 has a surface defined by ten intersecting planes to form sides 16 helically disposed about the axis "a" of projectile 10.

Figure 3:
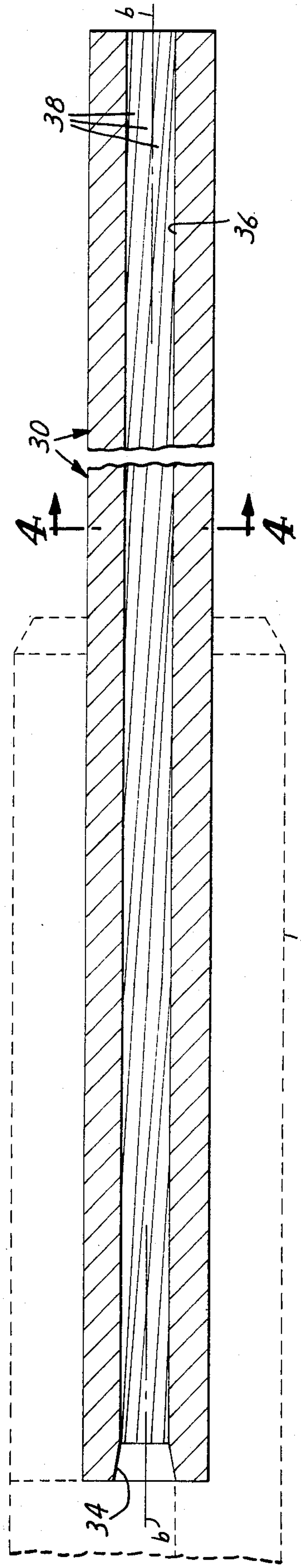
FIG. 3 is a top section view of a mounted barrel having a smooth helical polygonal bore complementary to the body of the projectile of FIG. 1.

As described hereinbefore, the body of the projectile is of a shape which can be inserted within the helical volume formed by the constant movement of a regular decagonal plane figure around and along axis "a" and wherein at least portions of the surface of the projectile body have the contour of the helical volume so formed. The projectile thus has an exterior surface having bearing portions which will bear upon the interior surface of the bore of a complementary barrel and will follow the helical path of the bore along the barrel. This allows the projectile to rotate about the longitudinal axis as it progresses along the barrel and will exit the barrel in a spinning mode. Preferably, the projectile will exit the barrel with sufficient rotational velocity to stabilize the projectile during flight. The rate of rotation can be controlled by the pitch of the helical surface of the projectile body and complementary bore as described hereinafter.

While projectile 10 is shown as having 10 sides which provide a body cross section having a regular decagonal perimeter, the body surface may comprise any number of sides from 3 up to about 20 or more. As a practical limit the maximum number of sides for a projectile having a diameter of about 0.25" (0.6 cm) should not be in excess of about 20 since beyond this point the perimeter of the cross section of the body approaches a circle and the projectile may have a tendency to ride over the sides of the bore of the barrel without achieving the desired rotational pattern for spin stabilization. The minimum number of sides on the projectile is dictated by stability considerations. A projectile having large sides tends to be more readily affected by air currents during flight. It is preferred to maintain the width of the sides within the range of about 0.04 inch (0.1 cm) to about0.15 inch (0.4 cm) and that the sides be of equal width. This corresponds to a range of about 5 to about 20 sides for a projectile having a nominal maximum diameter of about 0.25 inch (0.6 cm). For a body having sides of equal width the relationship is conveniently given by Standard mensuration formulae. When the body has sides of unequal width, it is preferred that the width of all of the sides fall within the range specified above, i.e. a width of between 0.1 cm and 0.4 cm.

As can be appreciated, the body surface of a larger diameter projectile can accommodate a greater number of sides, while a smaller diameter projectile must have fewer sides to maintain the preferred 0.04" (0.1 cm) minimum side width.

The pitch of the helically disposed sides of the projectile can be selected over a wide range, but the pitch should be selected to impart adequate flight stabilizing spin to the projectile. The pitch must be constant for each projectile. The pitch of the helix is the distance between two coils of the helix measured along the longitudinal axis of the body. In other words, the pitch is the distance in which one of the helically disposed sides of the body completes or would complete one full revolution around the body. Preferably the pitch is between 18 and 40 cm and is most preferably about 20–25 cm to provide a projectile having a "1 in 20" to "1 in 25" twist.

If the helical pitch of the projectile is greatly lengthened, the projectile will not achieve sufficient spin to be properly stabilized during flight. If the pitch is excessively short, the projectile will offer greater resistance to movement along a complementary bored barrel. Greater population forces will be needed to achieve the desired muzzle velocity. This condition may in turn produce increased friction forces in the barrel, resulting in objectionable wearing and fouling.

Figure 1:
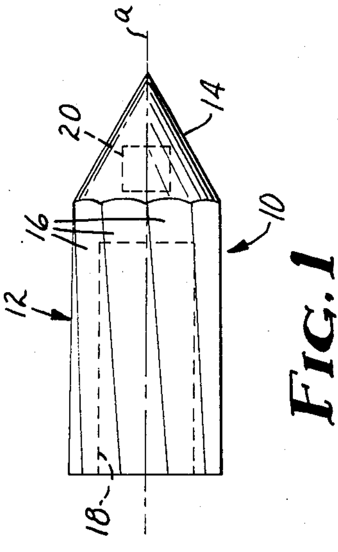
FIG. 1 is a side view of a projectile of the present invention showing optional cavities and ballast or labeling means in phantom.

Projectile 10 is shown in FIG. 1 as including a cavity defined by annular wall 18 opening to the rear of the projectile. The cavity is optional and can be used to carry a variety of beneficial payloads as will be described in greater detail hereinafter. Mass 20 is also shown embedded within projectile 10. The mass may be a ballast means, to stabilize the projectile during flight, or may be an active or passive identifying or labeling element such as the passive transponders, i.e., tuned, resonant circuits, described in copending applications U.S. Ser. No. 504,060 filed 9-9-74 now U.S. Pat. No. 4,065,753 and U.S. Ser. No. 504,059 filed 9-9-74 now U.S. Pat. No. 4,087,791, incorporated herein by reference.

Nose portion 14 is tapered to provide the desired flight and penetrating characteristics, depending on the preferred target. Various ogival designs, such as rounded and sharp pointed designs, are known in the conventional ballistics art and can be found in a variety of ballistic texts. These designs can be adapted for use with the projectiles of the present invention depending on the specific terminal ballistics characteristics desired.

Figure 2:
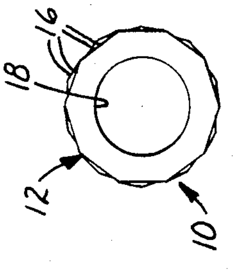
FIG. 2 is a rear view of the projectile shown in FIG. 1.

FIG. 2 is a rear view of the projectile 10 shown in FIG. 1, showing the cavity defined by annular wall 18 within body 12. Then helically disposed planes 17 form the sides of the surface of body 12.

FIG. 3 is a cross section view along the length of barrel 30 which is shown retained in mounting block 32. Barrel 30 comprises breech 34 and bore 36. The bore 36 is smooth, that is, the bore has no internal projections such as are characteristic of conventional land and groove barrels Rather, bore 36 comprises ten sides 38 helically disposed about the longitudinal axis "b" of bore 36. The diameter and pitch of helical bore 36 are complementary to the body surface of projectile 20 shown in FIG. 1. That is, the bore has a contour and dimensions identical to the imaginary helical volume circumscribing the projectiles which are to be propelled through the barrel. Thus, the bore 36 coincides with the volume formed by the rotation of the regular decagonal plane figure, as described with respect to projectile 10 hereinabove, around and along axis "b".

Projectile 10 can be propelled through barrel 30 whereby sides 16 of projectile 10 will contact and follow the complementary sides 38 of bore 36 so that as projectile 10 moves through barrel 30, the projectile is forced to rotate about longitudinal axis "a" and exits the muzzle of the barrel in a spinning mode.

Figure 4:
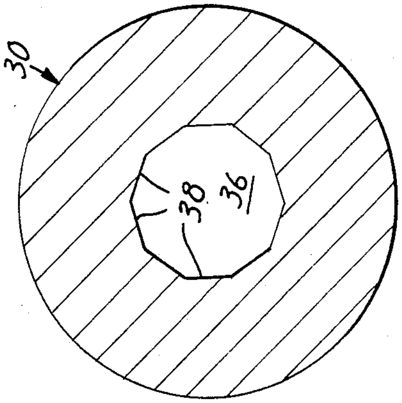
FIG. 4 is a cross section view along line 4—4 of the barrel of FIG. 3.

FIG. 4 is a cross section taken along line 4—4 of barrel 30. Bore 36 is shown having a decagonal perimeter formed by sides 38.

As noted hereinabove, the decagonal perimeter can be circumscribed by imaginary, extended, straight lines which coincide with the straight sides of the perimeter. All such extended lines will intersect at a point either on or outside of the perimeter. It is critical that the projectile bodies of this invention have helical surfaces which meet this requirement. Bodies having cross section perimeters wherein such lines intersect within the perimeter would have indentations therein. The complementary barrels would thus be required to have projections in the bore to mate with the projectile properly and would not be smooth bored as defined herein. This combination would produce objectionable fouling.

Figure 5:
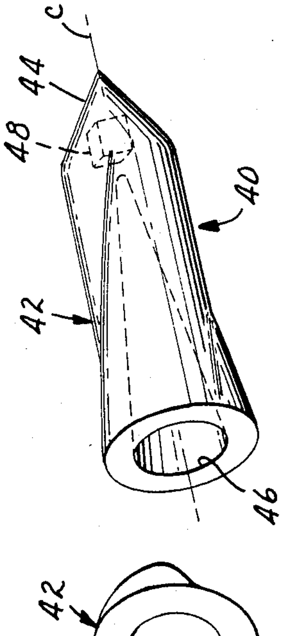
FIG. 5 is a perspective view of an alternative embodiment of a projectile showing optional cavities and ballast or labeling means partially in phantom.
Figure 6:
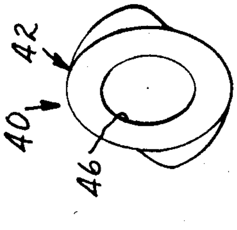
FIG. 6 is a rear view of the projectile shown in FIG. 5.

FIG. 5 is a perspective view showing an alternate embodiment of the invention wherein projectile 40 comprises a body portion 42 and a tapered nose portion 44. The cross section of body 42 is elliptical as shown by the rear view of projectile 40 (FIG. 6). The body 42 has a curved surface which is helically twisted about longitudinal axis "c". An optional cavity defined by annular wall 46 is shown opening to the rear of the projectile 40. This cavity may be used to carry and release, if desired, a variety of payloads. In addition, other means represented by cube 48, shown in phantom, can be incorporated in the projectile 40 to advantage as discussed with respect to the projectile shown in FIG. 1.

As described hereinbefore, the body of this projectile can be inscribed within the helical volume formed by the constant movement of an elliptical plane figure around and along axis "c" and wherein the surface of the projectile body has the contour of the helical volume so formed. The elliptical plane figure should have significantly different major and minor diameters so as to be non-circular and so that a spin about longitudinal axis "c" can be imparted when the projectile is propelled through a complementary barrel. The difference between the major and minor diameter should not be so great as to provide a projectile which will be excessively affected by air currents during flight. It is preferred that the length of the minor diameter be about 50 to 90% of the length of the major diameter. The requirements for the projectiles having curved surfaces are analogous to those for the projectiles having cross sections with polygonal perimeters as discussed with reference to FIG. 1 hereinabove.

Figure 7:
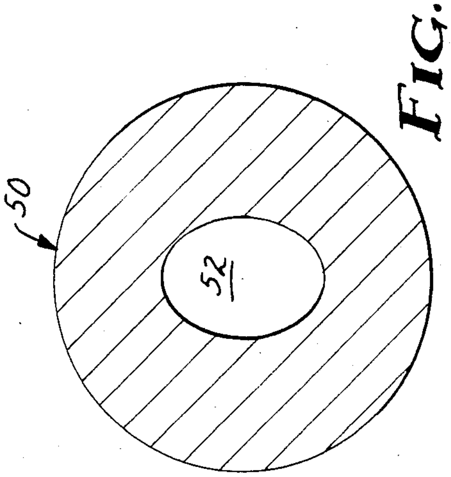
FIG. 7 is a cross section at a point along a barrel similar to that shown in FIG. 3 but having a smooth helically twisted bore complementary to the body of the projectile of FIG. 5.

FIG. 7 shows a cross section of a barrel similar to barrel 30 shown in FIG. 3, but having a smooth helical bore with curved walls 52 forming an elliptical perimeter. Barrel 50 is complementary in contour to the body of projectile 40 shown in FIG. 5 so that as projectile 40 is propelled through barrel 50, the projectile is caused to rotate about axis "c" and exit the muzzle of the barrel in a spinning mode.

As with the polygonal cross section perimeter shown in FIGS. 1–4, the elliptical perimeter of the projectile and bore in FIGS. 5–7 can be circumscribed by a series of imaginary extended straight lines tangent to the perimeter. For the reasons set forth with respect to the polygonal structures described herein, these lines must not intersect within the perimeter in order to be included within the structures contemplated by this invention.

Projectiles according to the present invention can be prepared from any material which has sufficient integrity to be formed into a projectile and propelled from a gun barrel at subsonic muzzle velocities without fracture. Further, the material must provide a finished projectile, including payload if any, which provides the necessary apparent density.

A variety of materials can be used to form the projectiles. Materials having a density below that of the heavy metals, such as lead, are preferred in order to provide the required mass characteristics. Generally organic materials are preferred, although certain lightweight metals, such as magnesium, can be used with advantage. The preferred organic materials are polymeric materials such as the various thermoplastic and thermosetting polymers.

When the projectiles of this invention are used to be impacted on, or implanted in, animals, it is preferred that a biomedically acceptable organic material is used. These materials can also be selected so as to be soluble or insoluble in the target animal body after ballistic implantation of the projectile. Exemplary of relatively insoluble materials are the synthetic organic polymers such as the polyolefins, e.g. polyethylene and polypropylene, polysiloxanes; polyamides, such as nylon; fluorinated hydrocarbon resins; ABS polymers and the like. Exemplary of polymers which are soluble in animal bodies, e.g. cattle, are the cellulose derivatives, such as hydroxy propyl cellulose available commercially under the tradename "Klucel" from the Hercules Powder Company.

Metallic projectiles can be used for certain applications. Magnesium is light in weight and can be dissolved by body fluids and thus projectiles of magnesium or combinations of magnesium and organic polymer, e.g. either the exterior or interior comprising magnesium, can be used. While lead is not a preferred material, lead may be incorporated into the projectile as a weight or ballast means or as a coating on the projectile. However, because of possible toxicity, lead is not generally desirable for implantation into an animal body where it can be exposed to the body, e.g. as a surface coating or in an otherwise soluble projectile. Moreover, projectiles having a surface coating of metallic lead have a greater tendency to smear and foul the barrel from which they are propelled due to the peculiar physical nature of lead. Accordingly, projectiles which have a surface substantially free of metallic lead are preferred for use in this invention.

A variety of inorganic fillers such as calcium carbonate, magnesium carbonate, ferric oxides, iron powder and the like can be used to alter the solubility properties and/or the density and other physical properties of the projectiles.

For certain applications it may be desired that the projectile rupture on impact with or without significant penetration, for example, to release a dye or a medicament, such as an antiseptic material or a tranquilizer. Certain waxes or fragile polymeric materials can be used to achieve these results with the whole projectile or only a portion thereof, such as the nose portion, made from the rupturable material.

Lubricants which may aid in the molding and shooting of the projectiles can be incorporated into the projectiles. Calcium stearate, glycerol monostearate, powdered teflon and the like can be used with advantage.

The projectiles of the present invention can be formed with internal cavities in which various types of beneficial payloads can be incorporated. The cavity may be left open or sealed with a removable, soluble or porous plug so that the payload can be disseminated following implantation into the animal. Various types of beneficial payloads and various means of providing sustained release of the payload can be employed such as are described in U.S. Pat. No. 3,948,263, issued Apr. 6, 1976, and U.S. Pat. No. 3,982,536, issued Sept. 28, 1976, the disclosures of which are incorporated herein by reference.

Of particular interest is the fabrication of completely soluble projectiles made from hydroxypropyl cellulose or other body-soluble polymer. The payload can be carried in a cavity in the body of the projectile or admixed and dispersed throughout the solid body of the projectile. After implantation, the projectile completely dissolves in the body, releasing its contents in the animal. Also of interest are the "solid dose" projectiles where the projectile comprises up to about 95% by weight active ingredient with the remainder being a biologically acceptable binder. Thus, projectiles comprising 90–95% penicillin and 5–10% hydroxypropyl cellulose binder can be molded into the shape of a projectile and used in accordance with this invention.

As noted previously herein, the projectiles of this invention can be propelled from complementary barrels without objectionable fouling even after extended use, e.g. several hundred shots. In contrast, projectiles prepared from similar materials which have round bodies, and which are propelled through conventional land and groove barrels to provide spin stabilization, show evidence of fouling after one hundred shots or less and must be periodically cleaned to provide maximum performance over an extended period of use. The projectiles of the present invention thus provide a distinct advantage over the known low density projectiles particularly under filed conditions where periodic cleaning is not practical.

The invention can be further illustrated by reference to the following examples.

EXAMPLE 1

Projectiles similar to that shown in FIG. 1 were prepared by injection molding technique. An intimate mixture of 50 parts hydroxypropylcellulose and 50 parts calcium carbonate was formed by dissolving the hydroxypropylcellulose in 250 parts methanol and stirring in the calcium carbonate to form a thick slurry. The solvent was removed by air drying and the resulting cake was crushed and used to injection mold projectiles using a decagon mold having a 25 cm helical pitch. The projectiles had an apparent density of about 2 $g/cm^3$.

These projectiles were propelled through a complementary barrel at subsonic muzzle velocities. After several hundred shots no objectional barrel fouling in the form of deposits in the barrel or significant loss of velocity occurred. When conventional round bodied projectiles were prepared from the same materials and propelled through a conventional, round land and groove barrel, the barrel showed evidence of fouling and required cleaning for extended use.

EXAMPLE 2

A 0.25 caliber (6.35 mm) projectile suitable for long term implantation in cattle and having a helical decagon body configuration similar to that shown in FIG. 1 was prepared from polyethylene by injection molding. A small passive transponder was inserted into the center cavity of the projectile. The remainder of the cavity was filled with epoxy resin which was cured in place and the projectile was then sterilized by exposure to ethylene oxide. The projectile had an apparent density of about 2.5 $g/cm^3$.

These projectiles could be propelled through a complementary decagon barrel without objectionable fouling. When implanted into cattle, the implant sites showed no adverse tissue reaction to the implant. The implanted transponder could be detected by remote electronic detection devices.

EXAMPLE 3

A projectile which can be dissolved or degraded in the tissue of animals was prepared by injection molding a projectile similar to that shown in FIG. 1, and having a cavity therein, from hydroxypropylcellulose. The decagon projectile was then sterilized with ethylene oxide. A pellet of dry vaccine (*Clostridium haemolyticum bacterin*) was pressed into the cavity. The loaded projectile had an apparent density of about 2 $g/cm^3$.

These projectiles could be propelled from a complementary decagon barrel without objectionable fouling of the barrel after hundreds of shots. When ballistically implanted into cattle, the projectile was found to have dissolved in the body in about 24 hours.

EXAMPLE 4

A projectile similar to that shown in FIG. 1 was prepared from a composition containing a high loading of penicillin. Ten parts of hydroxypropylcellulose was dissolved in 500 parts of methanol. 90 parts of potassium penicillin G was stirred into the liquid to form a homogeneous slurry. After air drying the slurry to remove the solvent, the caked mixture was finely ground. The resulting powders were then compacted into a helical decagon mold having a 25 cm pitch to provide projectiles with an apparent density of about 2 g/cm$^3$.

These projectiles could be propelled through a complementary decagon barrel without objectionable fouling. When implanted into cattle the projectile dissolved in the animal body within about 24 hours.

What is claimed is:

1. A ballistic projectile which can be propelled from a smooth bore barrel, thereby having spin about the longitudinal axis imparted thereto, said projectile comprising an elongated body portion and a tapered end portion, said projectile body having a configuration which is inscribed longitudinally within the volume enclosed by an imaginary solid helix generated by revolving a non-circular plane figure at a constant rate around an axis contained within and perpendicular to the plane of said figure while simultaneously moving said plane figure along said perpendicular axis at a constant rate, said plane figure having a perimeter wherein all imaginary, extended, straight lines circumscribing the perimeter of said plane figure intersect at points on or outside of said perimeter, at least the surface portions of said inscribed projectile body adjoining the surface of said helical volume having the contour of said helical volume, said projectile having an apparent density up to about 5 grams/cm$^3$.

2. A ballistic projectile according to claim 1 wherein said projectile body is constructed so that within said helical volume no open path exists which extends along the complete length of the projectile body.

3. A projectile according to claim 1 wherein said plane figure has a polygonal perimeter.

4. A projectile according to claim 3 wherein said polygonal perimeter is decagonal.

5. A projectile according to claim 1 wherein said plane figure has a substantially elliptical perimeter.

6. A projectile according to claim 1 wherein said body has a surface substantially free of metallic lead.

7. A projectile according to claim 1 wherein said body comprises a biomedically acceptable organic polymer.

8. A projectile according to claim 6 wherein said projectile contains a biologically active material.

9. A projectile according to claim 8 wherein said biologically active material is an antigen.

10. A projectile according to claim 8 including means for providing sustained release of said biologically active material.

11. A projectile according to claim 8 wherein said biologically active material is carried in a cavity in the body of said projectile.

12. A projectile according to claim 1 wherein said projectile is soluble in the fluids and cells of a living animal body.

13. A projectile according to claim 12 wherein a biologically active material is dispersed throughout said soluble projectile.

14. A projectile according to claim 13 wherein said biologically active material comprises up to 95% by weight, based on the total weight of the projectile, of biologically active material.

15. A projectile according to claim 1 containing a remotely detectable labeling means.

16. A projectile according to claim 15 wherein said labeling means comprises a transponder.

17. A ballistic system for propelling a projectile in a longitudinally oriented spinning mode comprising a projectile according to claim 1 contained within a barrel having a complementary, smooth, helical bore and means for propelling said projectile from said barrel.

18. A ballistic system according to claim 17 wherein said propulsion means is an expanding gas means.

19. A method for ballistically propelling a projectile from a barrel in a longitudinally oriented spinning mode without objectionable fouling of the barrel comprising (a) providing a projectile according to claim 1, (b) providing a barrel having a smooth helical bore complementary to said projectile, and (c) propelling said projectile through and out of said barrel by an expanding gas propulsion means.

20. A ballistically implantable projectile which can be propelled from a smooth bore barrel, thereby having spin about the longitudinal axis imparted thereto, said projectile comprising an elongated body portion and a tapered end portion, said projectile body having a configuration which is inscribed longitudinally within the volume enclosed by an imaginary solid helix generated by revolving a non-circular plane figure at a constant rate around an axis contained within and perpendicular to the plane of said figure while simultaneously moving said plane figure along said perpendicular axis at a constant rate, said plane figure having a perimeter wherein all imaginary, extended, straight lines circumscribing the perimeter of said plane figure intersect at points on or outside of said perimeter, at least the surface portions of said inscribed projectile body adjoining the surface of said helical volume having the contour of said helical volume, said projectile having an apparent density up to about 5 grams/cm$^3$.

* * * * *